US010215647B2

(12) United States Patent
Parasnis et al.

(10) Patent No.: US 10,215,647 B2
(45) Date of Patent: Feb. 26, 2019

(54) METHOD AND ASSEMBLY FOR DETERMINING THE TEMPERATURE OF A TEST SENSOR

(71) Applicant: Ascensia Diabetes Care Holdings AG, Basel (CH)

(72) Inventors: Narasinha Parasnis, Nanuet, NY (US); Hoi-Cheong Steve Sun, Mount Kisco, NY (US); Mu Wu, Hopewell Junction, NY (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 0 days.

(21) Appl. No.: 15/842,285

(22) Filed: Dec. 14, 2017

(65) Prior Publication Data

US 2018/0106688 A1    Apr. 19, 2018

Related U.S. Application Data

(63) Continuation of application No. 14/319,967, filed on Jun. 30, 2014, now Pat. No. 9,874,481, which is a
(Continued)

(51) Int. Cl.
*G01N 25/00* (2006.01)
*G01K 15/00* (2006.01)
(Continued)

(52) U.S. Cl.
CPC .......... *G01K 15/005* (2013.01); *A61B 5/1495* (2013.01); *A61B 5/14532* (2013.01);
(Continued)

(58) Field of Classification Search
None
See application file for complete search history.

(56) References Cited

U.S. PATENT DOCUMENTS 4,929,426 A    5/1990 Bodai et al. .................... 422/63
5,232,667 A    8/1993 Heib et al. ................. 422/82.04
(Continued)

FOREIGN PATENT DOCUMENTS

WO    WO 2009/119116 A1    10/2009    ............... G01K 7/00

OTHER PUBLICATIONS

PCT International Search Report for International Application No. PCT/US2010/037761 dated Oct. 29, 2010 (4 pages).
(Continued)

*Primary Examiner* — Lisa Caputo
*Assistant Examiner* — Nasir U Ahmed
(74) *Attorney, Agent, or Firm* — Nixon Peabody LLP

(57) ABSTRACT

Methods and systems accurately determine an analyte concentration in a fluid sample. In an example embodiment, a receiving port receives a test sensor. The test sensor includes a fluid-receiving area for receiving a fluid sample. The fluid-receiving area contains a reagent that produces a measurable reaction with an analyte in the fluid sample. The test sensor has a test-sensor temperature and the reagent has a reagent temperature. A measurement system measures the reaction between the reagent and the analyte. A temperature-measuring system measures the test sensor temperature when the test sensor is received into the receiving port. A concentration of the analyte in the fluid sample is determined according to the measurement of the reaction and the measurement of the test sensor temperature. A diagnostic system determines an accuracy of the temperature-measuring system. The calculation of the analyte concentration may be adjusted according to the accuracy of temperature-measuring system.

20 Claims, 10 Drawing Sheets

Related U.S. Application Data continuation of application No. 12/796,324, filed on Jun. 8, 2010, now Pat. No. 8,801,273.

(60) Provisional application No. 61/184,928, filed on Jun. 8, 2009.

(51) Int. Cl.
    *A61B 5/145*     (2006.01)
    *A61B 5/1495*     (2006.01)
    *G01N 21/84*     (2006.01)

(52) U.S. Cl.
    CPC ......... *G01N 21/8483* (2013.01); *G01N 25/00* (2013.01); *A61B 2560/0252* (2013.01); *A61B 2562/0295* (2013.01)

(56) References Cited

U.S. PATENT DOCUMENTS

| | | | |
|---|---|---|---|
| 5,626,139 A | 5/1997 | Szeles et al. | 128/664 |
| 5,972,715 A | 10/1999 | Celentano et al. | 436/164 |
| 6,364,524 B1 | 4/2002 | Markham | 374/131 |
| 6,367,972 B1 * | 4/2002 | Kamiyama | G01J 5/06 327/512 |
| 6,391,645 B1 | 5/2002 | Huang et al. | 436/95 |
| 6,880,968 B1 | 4/2005 | Haar | 374/131 |
| 7,494,816 B2 | 2/2009 | Burke et al. | 436/94 |
| 8,071,384 B2 | 12/2011 | Burke et al. | 436/14 |
| 8,105,841 B2 | 1/2012 | Blais et al. | 436/147 |
| 8,313,951 B2 | 11/2012 | Blais et al. | 436/147 |
| 8,801,273 B2 | 8/2014 | Parasnis et al. | 374/45 |
| 2003/0159945 A1 | 8/2003 | Miyazaki | 205/777.5 |
| 2004/0236244 A1 | 11/2004 | Allen et al. | 600/532 |
| 2009/0098657 A1 | 4/2009 | Blais et al. | 436/147 |
| 2009/0146826 A1 | 6/2009 | Gofman et al. | 340/636.2 |
| 2010/0159610 A1 | 6/2010 | Sun et al. | 436/147 |
| 2011/0191059 A1 | 8/2011 | Farrell et al. | 702/130 |
| 2014/0314117 A1 | 10/2014 | Parasnis et al. | 374/1 |

OTHER PUBLICATIONS

PCT International Written Opinion for International Application No. PCT/US2010/037761 dated Oct. 29, 2010 (5 pages).

* cited by examiner

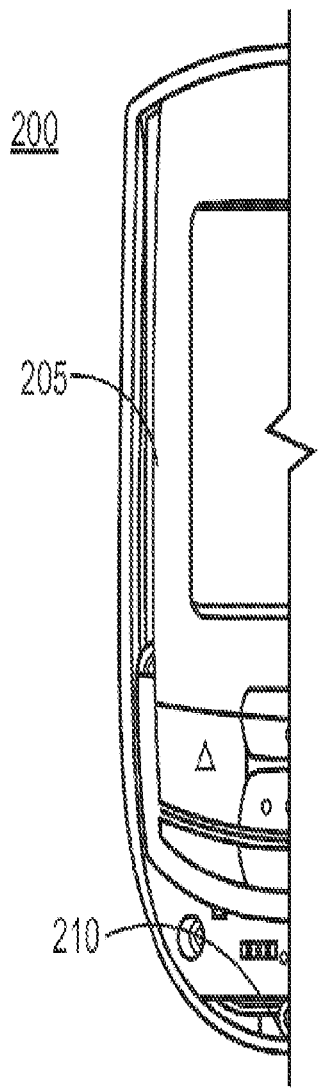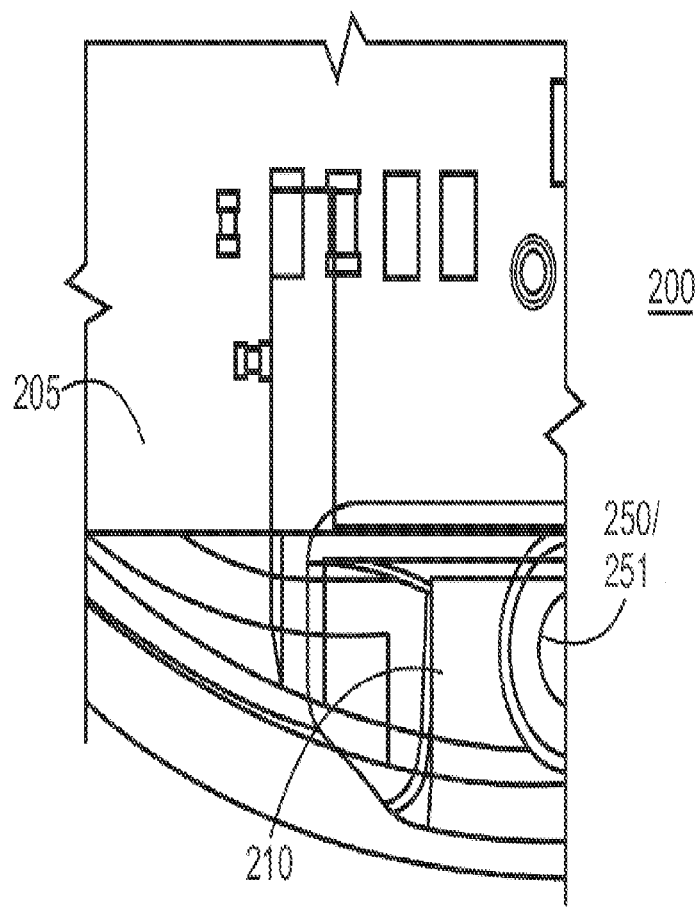
FIG. 3A
FIG. 3B

METHOD AND ASSEMBLY FOR DETERMINING THE TEMPERATURE OF A TEST SENSOR

CROSS REFERENCE TO RELATED APPLICATIONS

This application is a continuation of U.S. patent application Ser. No. 14/319,967, filed Jun. 30, 2014 now U.S. Pat. No. 9,874,481, which is a continuation of U.S. patent application Ser. No. 12/796,324, filed Jun. 8, 2010, now U.S. Pat. No. 8,801,273, which claims priority to and the benefits of U.S. Provisional Patent Application No. 61/184,928, filed Jun. 8, 2009, the contents of which are each hereby incorporated by reference herein in their entireties.

FIELD OF THE INVENTION

The present invention generally relates to a method and assembly for determining an analyte concentration in a sample of body fluid collected on a test sensor. Specifically, the present invention generally relates to a method and assembly for measuring the temperature of the test sensor to determine the temperature of a reagent reacting with the analyte and to achieve an accurate determination of the analyte concentration based on the reaction with the reagent. More specifically, the present invention generally relates to techniques for implementing and calibrating a temperature-measuring system to obtain more accurate and reliable temperature measurements of the test sensor.

BACKGROUND OF THE INVENTION

The quantitative determination of analytes in body fluids is of great importance in the diagnoses and maintenance of certain physiological abnormalities. For example, lactate, cholesterol and bilirubin are monitored in certain individuals. In particular, it is important that individuals with diabetes frequently check the glucose level in their body fluids to regulate the glucose intake in their diets. The results of such tests can be used to determine what, if any, insulin or other medication needs to be administered. In one type of blood-glucose testing system, test sensors are used to test a sample of blood.

A test sensor contains biosensing or reagent material that reacts with, for example, blood glucose. For example, the testing end of the sensor may be adapted to be placed into contact with the fluid being tested (e.g., blood) that has accumulated on a person's finger after the finger has been pricked. The fluid may be drawn into a capillary channel that extends in the sensor from the testing end to the reagent material by capillary action so that a sufficient amount of fluid to be tested is drawn into the sensor. The tests are typically performed using a meter that receives the test sensor into a test-sensor opening and applies optical or electrochemical testing methods.

The accuracy of such testing methods however may be affected by the temperature of the test sensor. For example, the result of the chemical reaction between blood glucose and a reagent on a test sensor may vary at different temperatures. To achieve an accurate reading, the actual measurement is corrected based on the actual sensor temperature, taken right before the reaction begins. The conventional way to measure the test sensor temperature involves reading a resistive value from a thermistor placed near the test-sensor opening. The thermistor resistance recalculates the chemical reaction result. This correction method is based on an assumption that a sensor temperature is the same as the thermistor temperature placed near the test-sensor opening. In reality, however, the thermistor, which is typically located on a printed circuit board, actually provides the temperature of the meter. Because the temperature of the meter can be very different from the test sensor temperature, the analyte measurement may be inaccurate.

SUMMARY OF THE INVENTION

Aspects of the present invention provide methods and assemblies for measuring the temperature of a reagent on a test sensor used to collect a sample of body fluid. The reagent reacts with an analyte in the sample of body fluid and the level of reaction may be measured to determine the concentration of analyte in the sample. The level of reaction may be affected by changes in temperature of the reagent. By determining a temperature for the reagent, aspects of the present invention account for the reagent's sensitivity to temperature and thus obtain a more accurate calculation of the concentration of analyte in the sample. Further aspects of the present invention provide techniques for implementing and calibrating a temperature-measuring system to obtain more accurate and reliable temperature measurements of the test sensor.

Accordingly, embodiments provide a device for determining an analyte concentration in a fluid sample. A receiving port receives a test sensor. The test sensor includes a fluid-receiving area for receiving a fluid sample. The fluid-receiving area contains a reagent that produces a measurable reaction with an analyte in the fluid sample. The test sensor has a test-sensor temperature and the reagent has a reagent temperature. A measurement system measures the reaction between the reagent and the analyte. A temperature-measuring system measures the test sensor temperature when the test sensor is received into the receiving port. A concentration of the analyte in the fluid sample is determined according to the measurement of the reaction and the measurement of the test sensor temperature. A diagnostic system determines an accuracy of the temperature-measuring system.

In an example embodiment, the diagnostic system above includes a reference object that achieves at least one reference temperature. The temperature-measuring system measures at least one test temperature for the reference object when the reference object achieves the at least one reference temperature. The diagnostic system determines the accuracy of the temperature-measuring system by comparing the at least one test temperature to the corresponding reference temperature. Furthermore, the device may be calibrated according to the accuracy of the temperature-measuring system.

Embodiments also provide a method for testing a meter. The meter determines an analyte concentration in a fluid sample collected on a test sensor by measuring a reaction between the analyte and a reagent on the test sensor. The meter includes a temperature-measuring system that determines a test sensor temperature. The meter uses the test sensor temperature as a parameter in determining the analyte concentration. The method includes the step of changing a temperature of a reference object to a specified reference temperature. The reference object is positioned in the meter for measurement by the temperature-measuring system. The method also includes the step of determining, with the temperature-measuring system, a test temperature for the reference object when the reference object achieves the reference temperature. Furthermore, the method includes the step of determining an accuracy of the temperature-measuring system by comparing the test temperature to the reference temperature.

These and other aspects of the present invention will become more apparent from the following detailed description of the preferred embodiments of the present invention when viewed in conjunction with the accompanying drawings.

BRIEF DESCRIPTION OF THE DRAWINGS

FIG. 3A illustrates a partial view of a meter according to aspects of the present invention.

FIG. 3B illustrates an enlarged transparent partial view of the meter of FIG. 3A.

Figure 1:
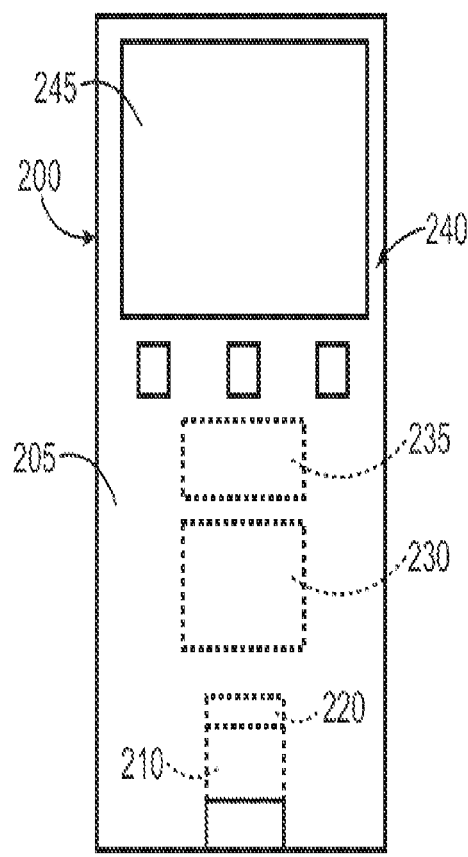
FIG. 1 illustrates a general diagnostic system, including a test sensor and a meter according to aspects of the present invention.
Figure 1:
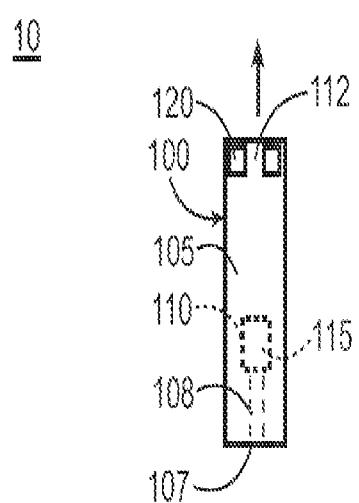

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION OF ILLUSTRATED EMBODIMENTS

Referring to FIG. 1, a test system 10 with a test sensor 100 and a meter 200 is illustrated. The test sensor 100 is configured to receive a fluid sample and in conjunction with the meter 200 help determine the concentration of a substance, such as an analyte, in the sample. Non-limiting examples of an analyte type include glucose, various lipids, microalbumin, hemoglobin and its derivatives, fructose, lactate, or bilirubin. Additional substances may also be tested using the methods described below. Non-limiting examples of a fluid sample include whole blood serum, whole blood, blood serum, blood plasma, urine and other body fluids such as interstitial fluid as well as non-body samples.

As shown in FIG. 1, the test sensor 100 includes a body 105 having a fluid-receiving area 110 for receiving a sample of body fluid. For example, a user may employ a lancet or a lancing device to pierce a finger or other area of the body to produce the blood sample at the skin surface. The user then collects this blood sample by placing an opening 107 of the test sensor 100 into contact with the sample. The blood sample flows from the opening 107 to the fluid-receiving area 110 via a capillary channel 108. The fluid-receiving area 110 contains a reagent 115 which reacts with the sample to indicate the concentration of an analyte in the sample. The test sensor 100 also has a meter-contact area 112 which is received by the meter 200 as described in detail further below.

The test sensor 100 may be an electrochemical test sensor, as is well known in the art. An electrochemical test sensor typically includes a plurality of electrodes and a fluid-receiving area that contains an enzyme. The fluid-receiving area includes a reagent for converting an analyte of interest (e.g., glucose) in a fluid sample (e.g., blood) into a chemical species that is electrochemically measurable, in terms of the electrical current it produces, by the components of the electrode pattern.

Alternatively, the test sensor 100 may be an optical test sensor, as is well known in the art. Optical test sensor systems may use techniques such as, for example, transmission spectroscopy, diffuse reflectance, or fluorescence spectroscopy for measuring the analyte concentration. An indicator reagent system and an analyte in a sample of body fluid are reacted to produce a chromatic reaction, as the reaction between the reagent and analyte causes the sample to change color. The degree of color change is indicative of the analyte concentration in the body fluid. The color change of the sample is evaluated to measure the absorbance level of the transmitted light.

As further illustrated in FIG. 1, the meter 200 includes a body portion 205 with a test sensor opening 210, which includes a connector for receiving and/or holding a test sensor 100. The meter 200 also includes a measurement system 220 for measuring the concentration of analyte for the sample in fluid-receiving area 110. For example, the measurement system 220 may include contacts for the electrodes to detect the electrochemical reaction for an electrochemical test sensor. Alternatively, the measurement system 220 may include an optical detector to detect the chromatic reaction for an optical test sensor. To process information from the measurement system 220 and to generally control the operation of the meter 200, the meter 200 employs computer processing hardware (processor) 230 which executes programmed instructions (on computer-readable media) according to a measurement algorithm. Data processed by the processing system 230 is stored in a conventional memory device 235, e.g., non-volatile memory. Furthermore, the meter has a user interface 240 which includes a display 245. Pushbuttons, a scroll wheel, touch screens, or any combination thereof, are also provided as a part of the user interface 240 to allow a user to interact with the meter 200. The display 245 typically shows information regarding the testing procedure and/or information in response to signals input by the user.

Diagnostic systems, such as blood-glucose testing systems, typically calculate the actual glucose value based on a measured output and the known reactivity of the reagent-sensing element (e.g., test sensor 100) used to perform the test. Calibration information is generally used to compensate for different characteristics of test sensors, which will vary on a batch-to-batch basis. The calibration information may be, for example, the lot specific reagent calibration information for the test sensor. The calibration information may be in the form of a calibration code. Selected information associated with the test sensor (which may vary on a batch-to-batch basis) is tested to determine the calibration information to be used in association with the meter. The reactivity or lot-calibration information of the test sensor may be provided on a calibration circuit that is associated with the sensor package or the test sensor. This calibration circuit may be inserted by the end user. In other cases, the calibration is automatically done using an auto-calibration circuit via a label on the sensor package or the test sensor. Embodiments of the present invention provide either a manual- or auto-calibrating diagnostic system. In the example shown in FIG. 1, the diagnostic system 10 is auto-calibrating, so the test sensor 100 may include an auto-calibration information area 120, which may include a label, at the meter-contact area 112.

Figure 2:
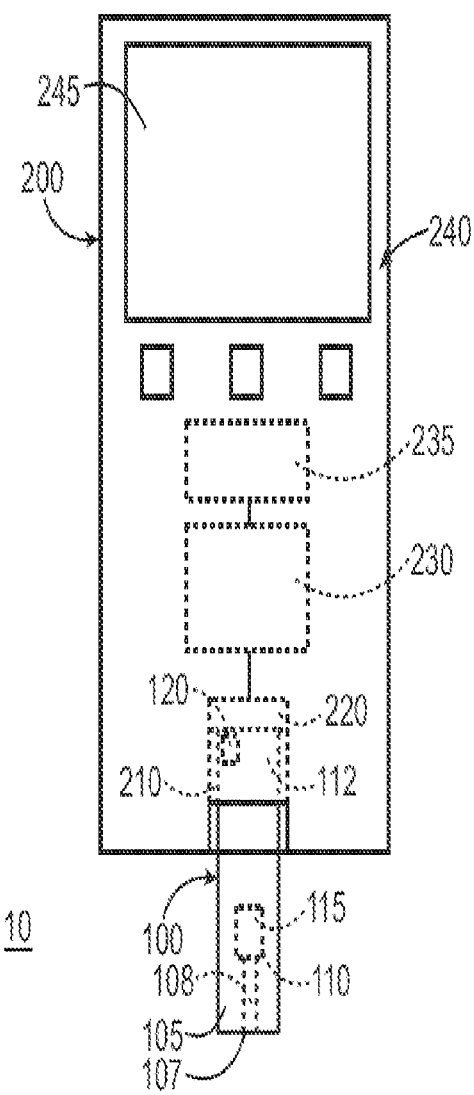
FIG. 2 illustrates the embodiment of FIG. 1 with the test sensor inserted into the meter.

Calibration of test sensors is required due to various factors. These factors include reagent sample size and manufacturing tolerances of the measurement system 220, such as electrode size, and separation dimension between adjacent electrodes. However, the temperature of the reagent on the test sensor 100 may also affect the accuracy of the concentration of analyte calculated by the meter 200, as the level of reaction between the analyte and the reagent 115 may be dependent on the temperature of the reagent 115. Generally speaking, a reagent will react differently with two equal samples if the temperature of the reagent is not equal. As such, embodiments of the present invention determine a temperature for the reagent 115 and use this calculated temperature to produce a more accurate measurement of the analyte concentration. In particular, the meter 200 has a temperature-measuring system 250 and the processing system 230 uses this calculated temperature from the temperature-measuring system 250 as a variable input for a measurement algorithm. The operation of the temperature-measuring system 250 and other aspects of the test system 10 shown in FIGS. 1 and 2 are described in U.S. patent application Ser. No. 12/252,348 titled "Method and Assembly for Determining the Temperature of a Test Sensor" and filed May 2, 2009, the contents of which are incorporated entirely herein by reference.

Figure 3C:
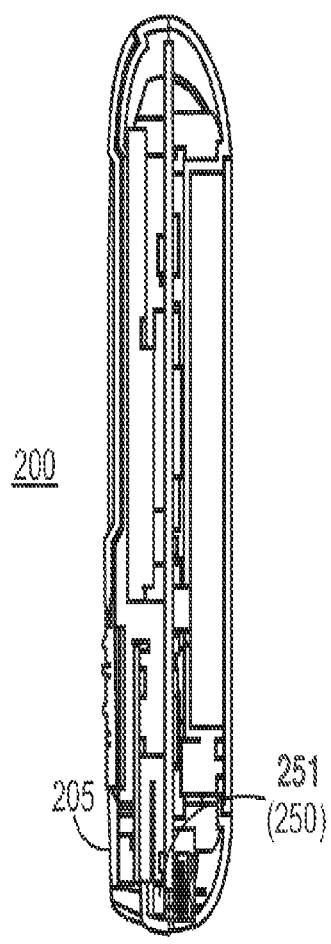
FIG. 3C illustrates an internal side view of the meter of FIG. 3A.
Figure 3D:
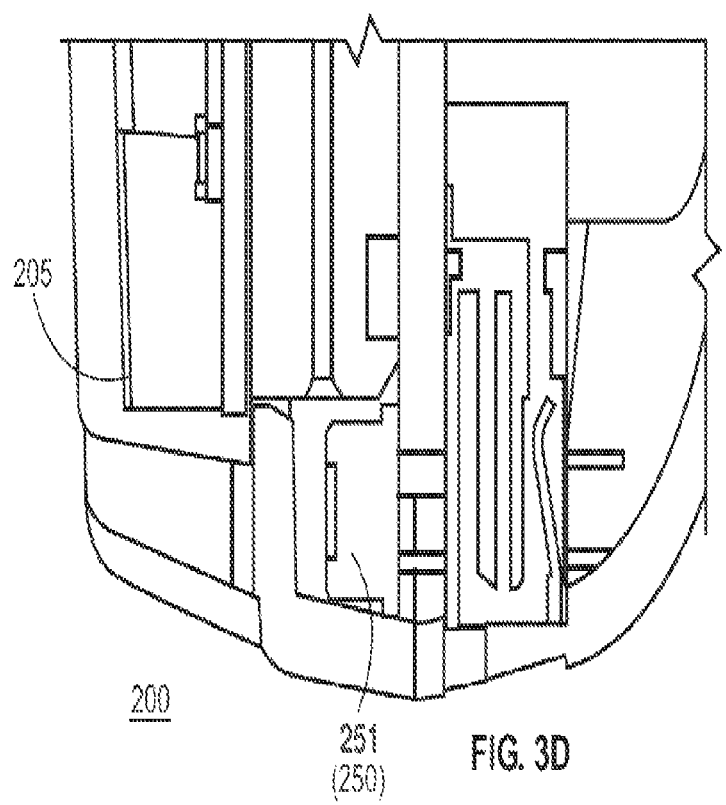
FIG. 3D illustrates yet another internal view of the meter of FIG. 3A.
Figure 3E:
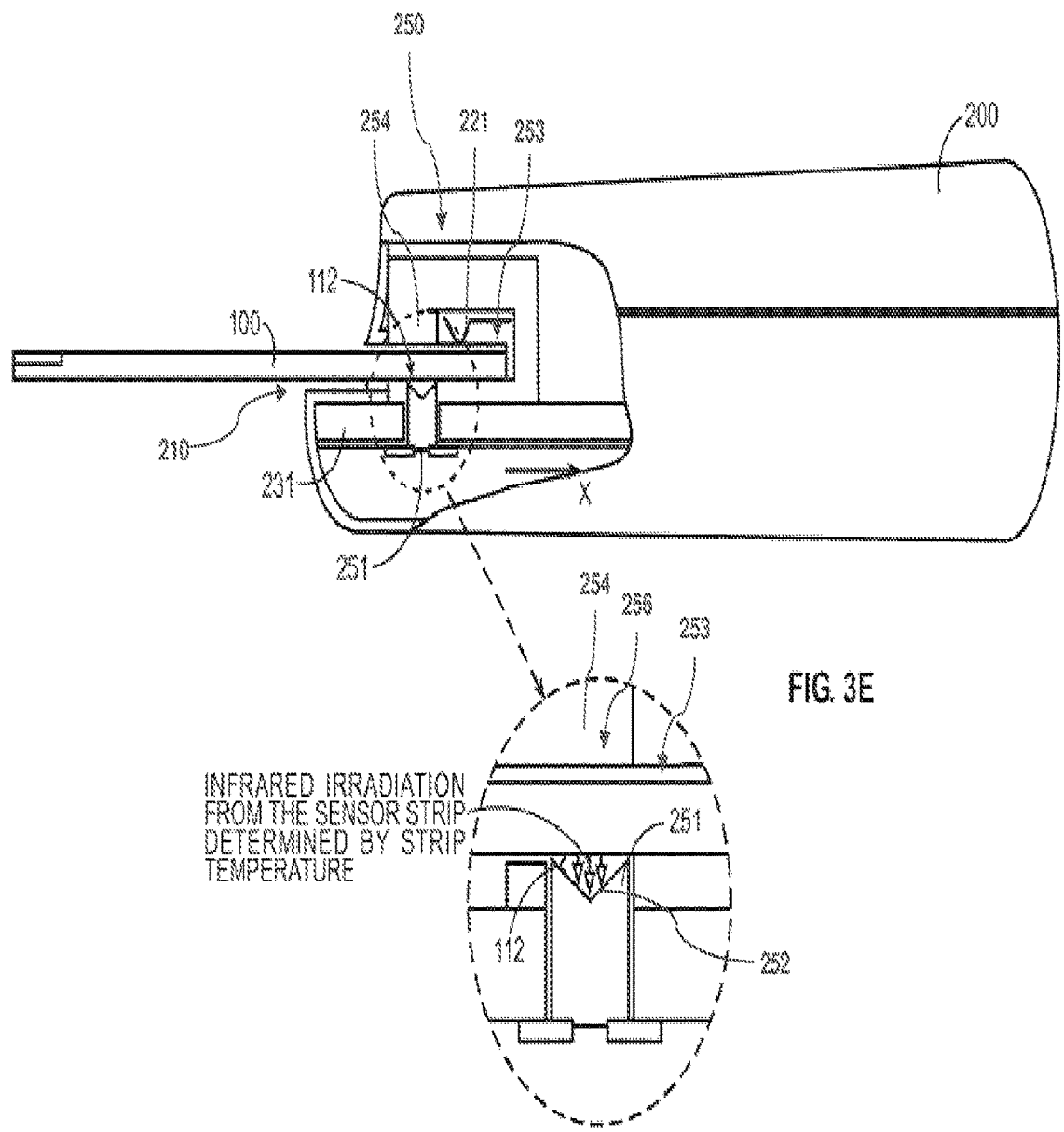
FIG. 3E illustrates yet another internal view of the meter of FIG. 3A.

In the embodiment illustrated by FIGS. 3A-E, the temperature-measuring system 250 includes a thermopile sensor 251 disposed at a position within the test-sensor opening 210 on a printed circuit board 231. As shown in FIG. 3E, the temperature-measuring system 250 is positioned in the test-sensor opening 210 of the meter body 205, such that the temperature-measuring system 250 is positioned in proximity to the test sensor 100 when it is inserted into the test-sensor opening (receiving port) 210.

Although some embodiments may include a temperature-measuring system 250 disposed at a position within the test-sensor opening 210, a temperature-measuring system 250 may be disposed at other areas to allow temperature measurement of test sensor 100. Moreover, other embodiments may include more than one structure disposed anywhere relative to the meter body 205 for measuring more than one area of the test sensor 100. Temperature measurements from more than one area may provide a more accurate determination of the temperature for the reagent 115.

In general, all materials at temperatures above absolute zero continuously emit energy. Infrared (IR) radiation is part of the electromagnetic spectrum and occupies frequencies between visible light and radio waves. The IR part of the spectrum spans wavelengths from about 0.7 micrometers to about 1000 micrometers. The wave band usually used for temperature measurement is from about 0.7 to about 20 micrometers. The thermopile sensor 251 measures the actual sensor strip temperature by using IR radiation emitted from the test sensor 100. By knowing the amount of IR energy emitted by the test sensor 100 and its emissivity, the actual temperature of the test sensor 100 can be determined. In particular, the thermopile sensor 251 generates a voltage proportional to incident IR radiation. Because the temperature of a surface of the test sensor 251 is related to the incident IR radiation, the temperature of the surface can be determined from the thermopile sensor 251.

When the test sensor 100 is received into the test-sensor opening 210, the position of the thermopile sensor 251 is proximate, or substantially adjacent, to the test sensor 100. The position ensures that the IR radiation detected by the thermopile sensor 251 comes substantially from the test sensor 100. In other words, the thermopile sensor 251 is positioned to minimize the effect of light from external sources, e.g., ambient light, on the readings of the thermopile sensor 251. As shown in FIG. 3E, the thermopile sensor 251 includes a detecting surface 252 that faces the meter-contact area 112 and receives the IR radiation from the test sensor 100 positioned in the meter 200. While FIG. 3E shows the thermopile sensor 251 below the test sensor 100, it is understood that the thermopile sensor 251 may be positioned in other appropriate positions relative to the test sensor.

Figure 3F:
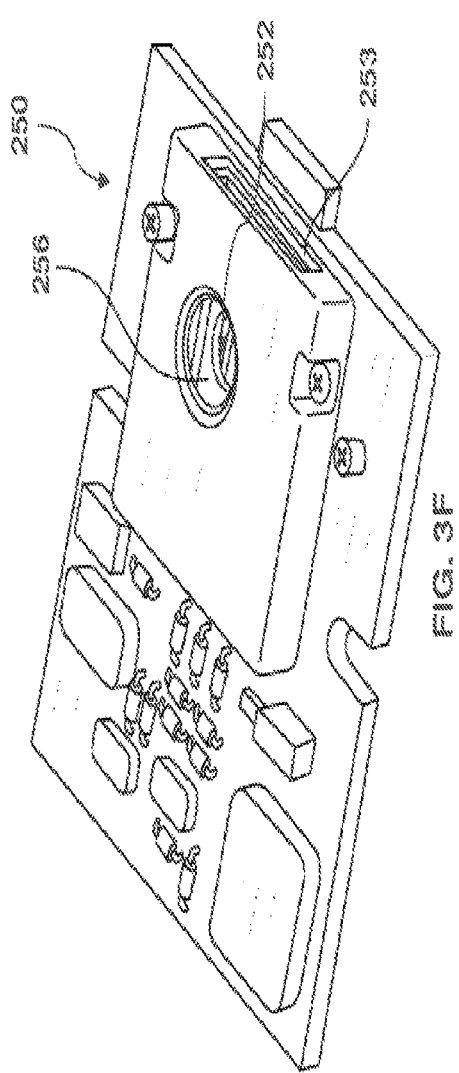
FIG. 3F illustrates a temperature-measuring system that may be employed with the meter of FIG. 3A according to aspects of the present invention.
Figure 3G:
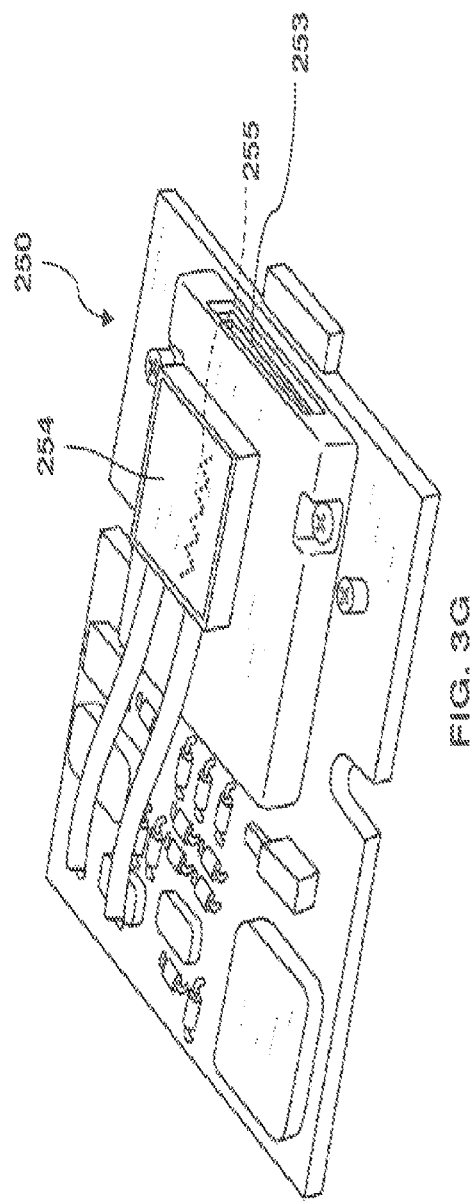
FIG. 3G illustrates an embodiment of the temperature-measuring system of FIG. 3F.

As shown in FIGS. 3F-G, the temperature-measuring system 250 includes a receiving port 253. The receiving port 253 is aligned with the test-sensor opening 210, so that the receiving port 253 receives the meter-contact area 112 of the test sensor 100 when the test sensor 100 is inserted into the test-sensor opening 210. The thermopile sensor 251 is positioned relative to the receiving port 253 so that it can access the meter-contact area 112 for measurement when the test sensor 100 is received by the receiving port 253.

Figure 3H:
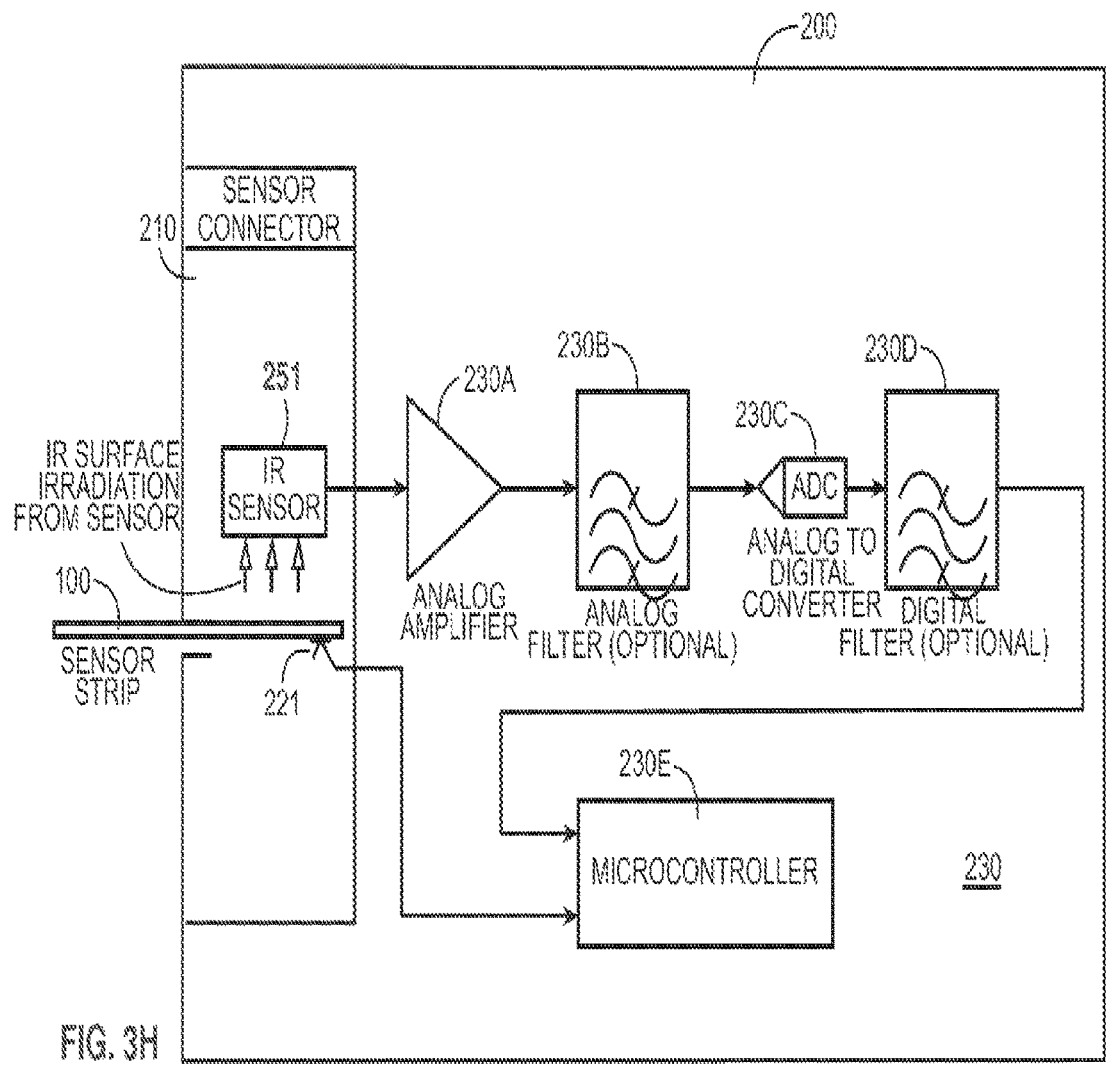
FIG. 3H illustrates an example processing system for the meter of FIG. 3A.

FIG. 3H illustrates aspects of a processing system 230 that are employed for implementing the thermopile sensor 251 in the meter 200. First, an output electrical signal from the thermopile sensor 251 is received by an analog amplifier 230A. The amplified analog signal from the analog amplifier 230A is passed to an analog-to-digital converter 230C via an analog filter 230B. The analog-to-digital converter 230C digitizes the amplified analog signal, which may subsequently be filtered by a digital filter 230D. The digital signal is then transmitted to a microcontroller 230E. The microcontroller 230E calculates the temperature of the test sensor 100 based on the magnitude of the output electrical signal from the thermopile sensor 251 and the calculated temperature is employed to correct the initial blood glucose measurement from the measurement system 220. For some embodiments, it is contemplated that the analog filter 230B, the analog-to-digital converter 230C, and the digital filter 230D may be incorporated into the microcontroller 230E. In some embodiments, the analog filter 230B and the analog-to-digital converter 230C may be integrated into an application-specific integrated circuit (ASIC). In further embodiments, a memory, such as an EEPROM, may be employed to store calibration data and the like. Moreover, it is further contemplated that in some embodiments the analog filter 230B and the digital filter 230D may be optional. It is also noted that although the thermopile sensor 251 in FIG. 3E is positioned opposite from the electrical contacts 221 that receive the test sensor electrodes, other embodiments may position the thermopile sensor to be on the same side of the test sensor.

The use of a thermopile sensor to measure the temperature of the test sensor is further described in U.S. patent application Ser. No. 12/252,348 titled "Method and Assembly for Determining the Temperature of a Test Sensor" and filed May 2, 2009, the contents of which are incorporated entirely herein by reference. The accuracy of such systems may be further improved if aspects of the temperature-measuring system are also calibrated. Thus, embodiments of the present invention provide improved techniques for implementing and calibrating a temperature-measuring system to obtain more accurate and reliable temperature measurements of the test sensor.

For example, embodiments may achieve further accuracy for temperature measurements by employing a diagnostic system that detects the existence of conditions that may affect accuracy. Tests have shown that environmental conditions can have a significant effect on the temperature measurement by a thermopile sensor. In particular, condensation, dust, and dirt on the detecting surface of the sensor may cause the thermopile sensor to read the temperature of an object, such as a test sensor, incorrectly. To address such situations, the temperature-measuring system 250 may include a reference object 254, as shown in FIGS. 3E and G. In general, the reference object 254 provides a technique for testing the accuracy of the thermopile sensor 251. The reference object 254 may be a structure originally designed as a part of the meter 200 or may be a structure that is specifically designed and dedicated for testing and calibration of the thermopile sensor 251.

As further illustrated in FIG. 3F, the temperature-measuring system 250 may include a window, or aperture, 256. FIG. 3G shows the reference object 254 positioned at the window 256. The window 256 is aligned with the detecting surface 252 of the thermopile sensor 251. The reference object 254 is positioned relative to the window 256, so that the thermopile sensor 251 is able to view the reference object 254 via the window 256 when a test sensor 100 is not positioned within receiving port 253. Because the reference object 254 is in the field-of-view (FOV) of the thermopile sensor 251, the thermopile sensor 251 can measure the IR radiation of reference object 254. In alternative embodiments, a window 256 is not necessary to provide the thermopile sensor 251 with a view of the reference object 254.

The reference object 254 is controlled to reach a known, constant temperature. As shown in FIG. 3G, the reference object 254 includes a resistor 255 that reaches a known, constant temperature when it receives a current. When subject to the specified current, the resistor 255 reaches a constant temperature each time and therefore emits the same amount of IR radiation each time. The known, constant temperature provides a reference temperature by which the temperature-measuring system 250 may be tested and calibrated.

Figure 4:
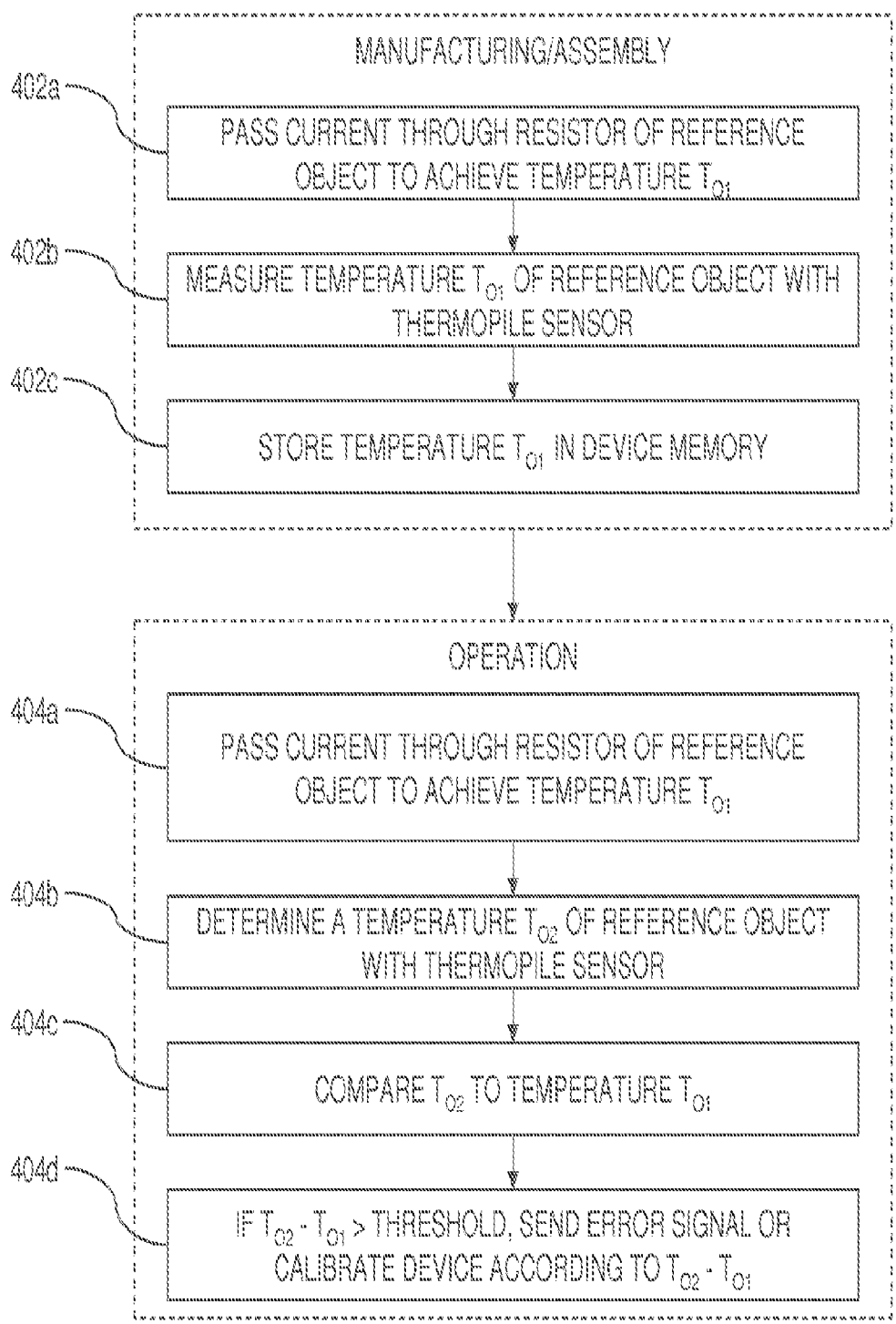
FIG. 4 illustrates an example of a diagnostic test for a temperature-sensing system according to aspects of the present invention.

An approach for employing the reference object 254 is illustrated in FIG. 4. In acts 402a-c, reference measurements may be taken from the thermopile sensor 251 during the manufacturing or assembly process. In particular, in act 402a, a specified current is passed through the resistor 255 associated with the thermopile sensor 251. In act 402b, the thermopile sensor 251 measures the IR radiation emitted from the reference object 254 in its FOV to obtain a temperature $T_{O1}$ for the reference object 254. In act 402c, the measurement $T_{O1}$ is stored in memory and is used as reference data for testing and calibration.

During operation, the assembled meter 200 periodically wakes up the thermopile sensor 251 according to a timing algorithm to perform a diagnostic test according to steps 404a-d in FIG. 4. In act 404a, the current specified during manufacturing is passed through the resistor 255 associated with the thermopile sensor 251 to achieve reference temperature $T_{O1}$. In act 404b, the thermopile sensor 251 measures the IR radiation emitted from the reference object 254 in its FOV to obtain a test temperature $T_{O2}$ for the reference object 254. Then, in act 404c, the test temperature $T_{O2}$ is compared to the reference temperature $T_{O1}$ retrieved from the memory. In act 404d, a signal is issued indicating the results of the comparison. For example, if a metric representing the difference between the test temperature $T_{O2}$ and the reference temperature $T_{O1}$ is greater than a predefined threshold, it is assumed that the thermopile sensor 251 is not functioning optimally, e.g., the detecting surface 252 of the thermopile sensor 251 is damaged or obstructed. In response, the thermopile sensor 251 may be further calibrated to adjust for the non-optimal operation of the thermopile sensor 251. For example, data for adjusting the measurements from the thermopile sensor 251 for a particular difference between $T_{O1}$ and $T_{O2}$ may be predetermined and also stored in the memory.

Alternatively, rather than measuring a known, constant temperature, other embodiments may measure the rate of heat change of the reference object 254 as the resistor 255 receives current. If the rate of heat change measured by the thermopile sensor 251 does not substantially match the expected rate of heat change (reference data), it is assumed that the thermopile sensor 251 is not functioning optimally and the thermopile sensor 251 can be correspondingly calibrated.

Figure 5:
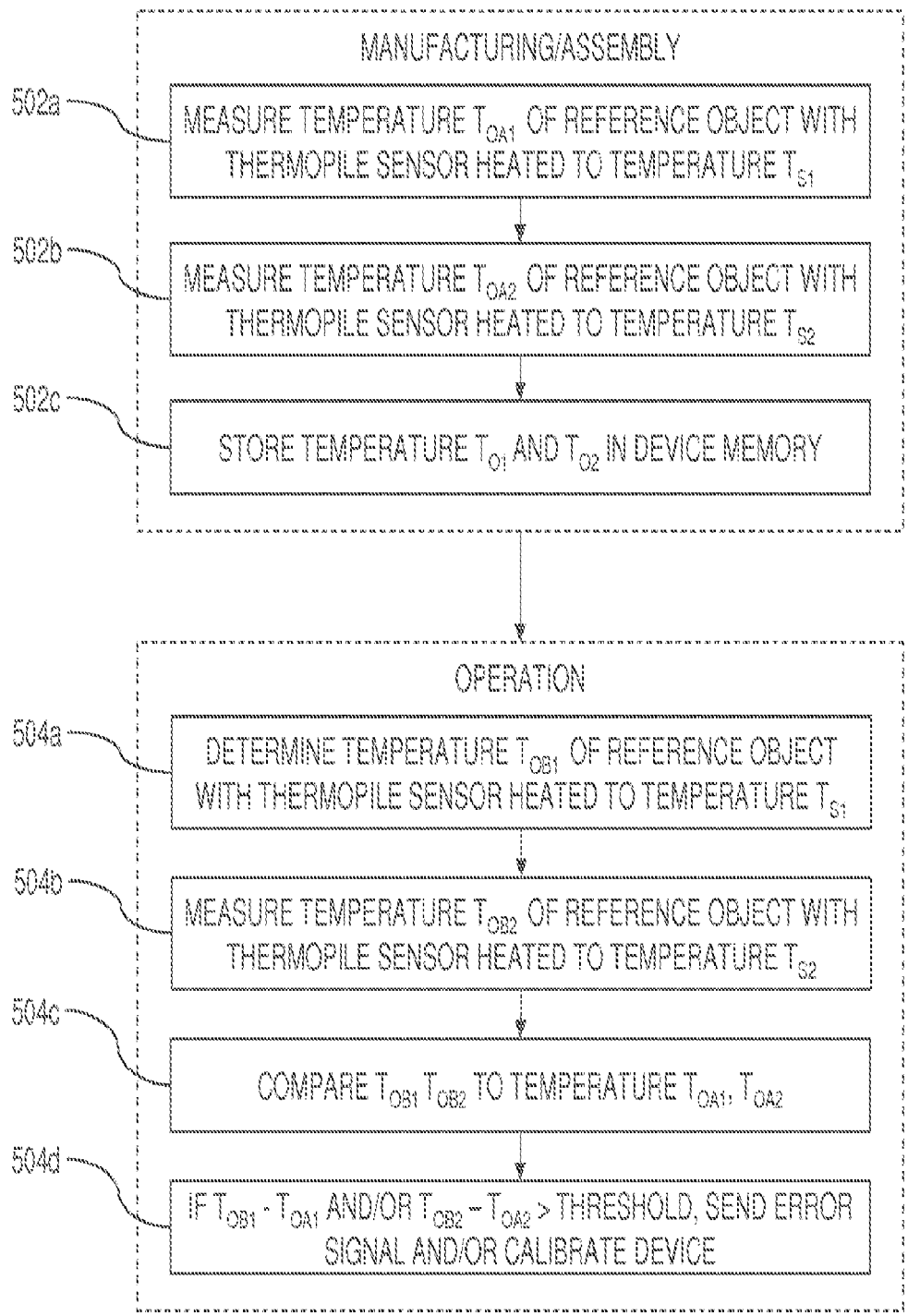
FIG. 5 illustrates another example of a diagnostic test for a temperature-measuring system according to aspects of the present invention.

To heat the reference object 254 to a known, constant temperature, other embodiments may heat the body of the thermopile sensor 251, which is proximate to the reference object 254. Referring to FIG. 5, another diagnostic test for the thermopile sensor 251 is illustrated. In acts 502a-c, reference measurements may be taken from the thermopile sensor 251 during the manufacturing or assembly process. In particular, in step 502a, the thermopile sensor 251 measures the temperature $T_{OA1}$ of the reference object 254 in its FOV while the body of the thermopile sensor is heated to a temperature $T_{S1}$. Then, in act 502b, the thermopile sensor 251 measures the temperature $T_{OA2}$ of the reference object 254 while the body of the thermopile sensor 251 is at a different temperature $T_{S2}$. The body of the thermopile sensor 251 may be heated by an internal or external active electrical circuit to achieve temperatures $T_{S1}$ and $T_{S2}$. For example, the circuit may include a heating element similar to the resistor 255 described previously. In act 502c, the measurements $T_{OA1}$ and $T_{OA2}$ are stored in memory and are used as reference data for testing and calibration.

During operation, the assembled meter 200 periodically wakes up the thermopile sensor 251 according to a timing algorithm to perform the diagnostic test according to steps 504a-c in FIG. 5. In act 504a, the thermopile sensor 251 measures the test temperature $T_{OB1}$ of the reference object 254 in its field of view (FOV) while the body of the thermopile sensor 251 is at temperature $T_{S1}$ specified during the manufacturing process at act 502a. Then, in act 504b, the thermopile sensor 251 measures the test temperature $T_{OB2}$ of the reference object 254 while the body of the thermopile sensor 251 is at a different temperature $T_{S2}$ specified during the manufacturing process at act 502b. In act 504c, the test temperatures $T_{OB1}$ and $T_{OB2}$ are compared to the reference temperatures $T_{OA1}$ and $T_{OA2}$. In act 504d, a signal is issued indicating the results of the comparison. For example, if a metric representing the differences between the test temperatures $T_{OB1}$ and $T_{OB2}$ and the reference temperatures $T_{OA1}$ and $T_{OA2}$ is greater than a predefined threshold, an error signal is issued. In this case, it is assumed that the thermopile sensor 251 is not functioning optimally. If the thermopile sensor 251 is covered with dust, for example, the thermopile sensor 251 measures a test temperature that is higher than the reference temperature of the reference object, because the thermopile sensor 251 is also detecting the temperature of the dust. The dust is in contact with the body of the thermopile sensor 251 and thus has a temperature closer to that of the body of the thermopile sensor and generally greater than that of the reference object, which is not in contact with the thermopile sensor. In response, the thermopile sensor 251 may be further calibrated to adjust for the non-optimal operation of the thermopile sensor 251. For example, data for adjusting the measurements from the thermopile sensor 251 for differences between the reference and test temperatures may be predetermined and also stored in the memory. FIG. 5 illustrates that more than one reference temperature may be employed to test the temperature-measuring system 250.

Figure 6:
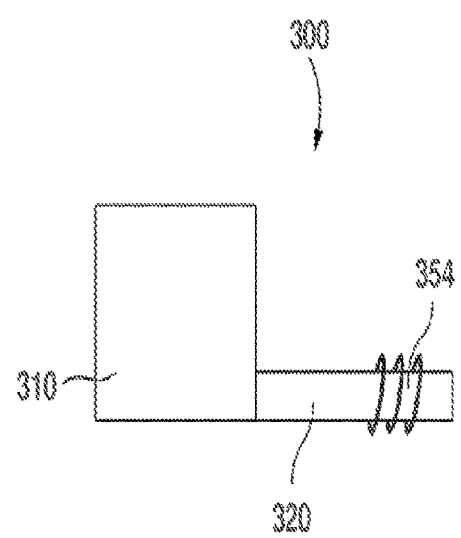
FIG. 6 illustrates a view of a calibration device that may be employed to conduct a diagnostic test of a temperature-measuring system according to aspects of the present invention.

As an alternative, instead of employing a reference object that is integrated or attached to the meter, the reference object may be provided on a separate calibration device that is removably inserted into the meter. For example, such a calibration device 300 is illustrated in FIG. 6. The calibration device 300 includes a heating element 310 and a flange 320. The flange 320, which extends from the heating element 310, may be similar in shape to a test sensor to permit insertion into the test-sensor opening. As FIG. 6 illustrates, the flange 320 includes a reference object 354, which performs the same function as the reference object 254 described previously. The reference object 330 is coupled to the heating element 310, which may be powered using an internal power source, power from the meter, or an alternate power source. Accordingly, at regular intervals or time periods, a user may insert the calibration device 300 into the meter, which may also be similar to the meter 200 described previously. Like a test sensor, the flange 320 is inserted into the test sensor opening of the meter and into the receiving port of a temperature-measuring system. The reference object 354 is positioned proximate the thermopile sensor of the temperature-measuring system, i.e., within the field-of-view of the thermopile sensor. As power is delivered to the heating element 310, the reference object 354 reaches a known, constant temperature or experiences changes in temperature at a known rate. The IR radiation emitted from the reference object 354 is measured by thermopile sensor. If the measured quantity of IR radiation does not correspond to the temperature characteristics of the reference object 354, it is assumed that the thermopile sensor is not functioning optimally and the thermopile sensor is calibrated to adjust for the change in functionality.

Although the embodiments described above may employ resistors as heating elements, other types of heating elements may be employed according to aspects of the present invention. For example, an IR diode or IR LED may be employed. Alternatively, a visible spectrum LED may be employed, where the LED is driven with relatively high current. The visible spectrum LED may provide illumination of the test sensor opening while also providing a heating element for testing and calibrating the thermopile sensor. It is further understood that the heating elements described herein only represent an example of how the temperature of the reference object may be controlled. Alternatively, the temperature of the reference object may be controlled with a cooling element that cools the reference object to a reference temperature.

Figure 7:
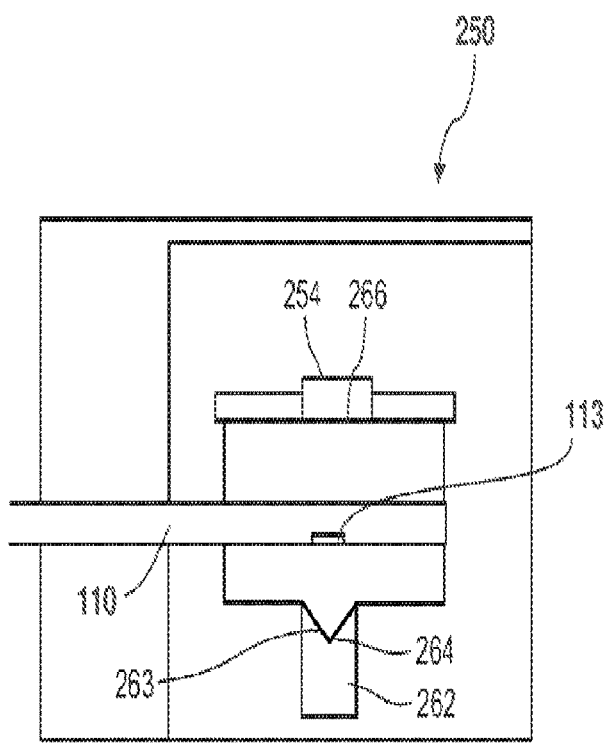
FIG. 7 illustrates a temperature-measuring system that may be employed with a meter according to aspects of the present invention.

Furthermore, although embodiments described herein may employ thermopile sensors, which measure IR radiation to determine temperature, the temperature-measuring system 250 of other embodiments employ an optical-sensing system 262, as illustrated in FIG. 7. Rather than measuring IR radiation, the temperature-measuring system 250 may determine temperature by measuring light reflected from a thermochromic material. The use of thermochromic materials are described, for example, in U.S. patent application Ser. No. 12/252,348, titled "Method and Assembly for Determining the Temperature of a Test Sensor" and filed May 2, 2009, the contents of which are incorporated entirely herein by reference. As shown in FIG. 7, the test sensor 110 includes a thermochromic material 113, which indicates the temperature of the test sensor 110. The optical-sensing system 262 includes a light source 263 and a light detector 264. The light source 263 directs photons at the thermochromic material 113 and the light detector 264 collects reflected photons to determine the temperature of the test sensor 110. According to aspects of the present invention, a thermochromic material 266 may also be applied to a reference object 254, which is in the FOV of the optical-sensing system 262. Although the reference object 254 in FIG. 7 may be a part of the meter, it may also be provided on a removably insertable calibration device as shown in FIG. 6. The temperature of the reference object 254 may be controlled to achieve a reference temperature as described previously, and the optical-sensing system 262 is diagnostically tested by comparing the test temperature measured by the optical-sensing system 262 and the reference temperature.

In general, the diagnostic test detects conditions, e.g., environmental contaminants or component failure, that cause a thermopile sensor to measure incorrect temperatures relative to reference calibration measurements. Advantageously, implementing a diagnostic test as described previously provides closed-loop control of temperature measurement by a thermopile sensor and helps to maintain the integrity of the temperature measurement.

According to aspects of the present invention, the temperature-measuring system may be further calibrated to achieve more accurate temperature measurements. In further embodiments, the temperature-measuring system is calibrated to correct for offset and gain errors that occur in processing the signal. In particular, offset and gain errors may be associated with any precision operational amplifiers that are used to amplify the signal of the thermopile sensor. In addition, the temperature-measuring system may be calibrated to account for the configuration associated mechanical alignment of the thermopile sensor as well as the field-of-view, aperture size, etc.

Operational amplifiers may be interfaced with the thermopile sensor as separate components during assembly of the meter, and calibration may be performed after the meter has been completely assembled. For example, each assembly may be calibrated by exposing the active area of the thermopile sensor to a black body target. Complete assembly is generally required before calibration, because the operational amplifiers which are interfaced with the thermopile sensor can also contribute to gain, offset, and non-linearity errors that affect the temperature reading. It is often difficult, however, to calibrate for the thermopile sensor and operational amplifiers after the meter is completely assembled. To achieve accurate calibration, the thermopile sensor must be exposed to a precisely controlled target. More specifically, the surface radiation intensity of the target must be precisely controlled. The thermopile sensor is configured to measure the temperature of a test sensor upon assembly of the meter, and the geometry of the test sensor port/connector makes it very difficult to perform accurate calibration and to meet regulatory standards, e.g., FDA standards.

Figure 8:
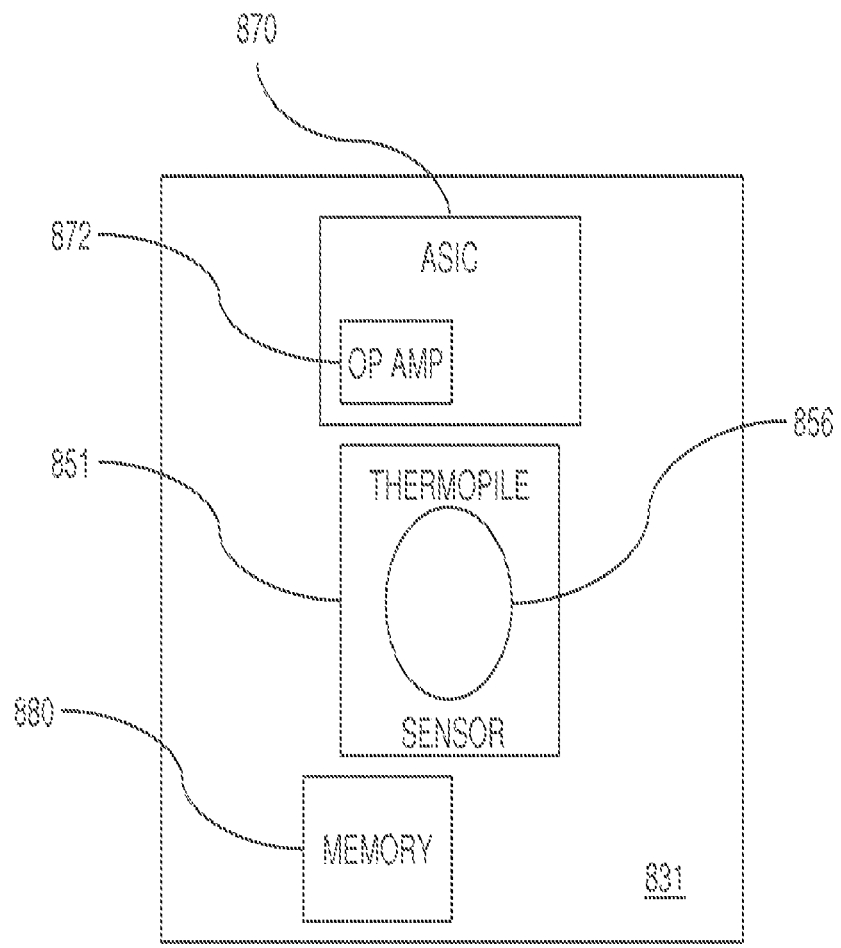
FIG. 8 illustrates an example of an integrated temperature measurement module according to aspects of the present invention.

Aspects of the present invention provide an improved technique for calibrating the temperature-measuring system during assembly of the meter. Accordingly, as shown in FIG. 8, a meter employs a temperature measurement module (e.g. chip package) 831. The temperature measurement module 831 includes a thermopile sensor 851 with a built-in ASIC 870 which provides a preamplifier 872 for the thermopile sensor 851. In some cases, the interface to the temperature measurement module 831 is simplified, so that the interface with external circuits does not introduce large error. Accordingly, all the components that make calibration necessary, i.e., the thermopile sensor 851 and the ASIC preamplifier 872, are pre-assembled into the temperature measurement module 831.

The characteristics of the temperature measurement module 831 are determined, at least in part, by (1) the relative position between the thermopile sensor 851 and the aperture 856 through which the IR radiation is detected; and (2) the manner in which the thermopile sensor 851 is connected to and paired with the ASIC 870.

As FIG. 8 further illustrates, the temperature measurement module 831 also includes an integrated memory 880, which can store the calibration data. Thus, the temperature measurement module 831 includes all three necessary electrical components for a functioning temperature-measuring system: (1) the thermopile sensor 851, (2) the ASIC preamplifier 872, and (3) the memory 880. The memory 880, for example, may be a semiconductor memory chip, such as an EEPROM, or a one-time programmable (OTP) memory. The memory 880 provides extra memory to store system algorithm constants. The information on the memory 880 may include, but is not limited to: sensor serial number, data format identifier, production lot identification, sensor characteristic profile, sensor calibration, and checksum. In some cases, it is advantageous to make the information on the memory 880 readable only after the temperature measurement module 831 has been assembled into the meter.

Incorporating the memory 880 in the temperature measurement module 831 provides a high level of integration that makes it possible to calibrate for the thermopile sensor 851 and the ASIC preamplifier 872 and to store the calibration data in the memory 880 before the temperature measurement module 831 is installed in the meter. In other words, the temperature measurement module 831, rather than the assembled meter, is more easily calibrated with a blackbody and modeled, for example, to a third-order polynomial. In addition, all information relating to temperature measurement may be stored on the temperature measurement module 831. The temperature-measuring system 250 shown in FIGS. 4 and 5 may be calibrated as a part of the temperature measurement module 831, and the reference temperatures may be stored in the memory 880. Thus, calibration can be completed at an early stage of the manufacturing process. Cost savings can be realized for the assembler of the meter, who is not required to perform any calibration after assembly. Furthermore, it is possible to integrate all the functional blocks onto a single semiconductor chip to reduce the size of and the cost of implementing the temperature measurement module 831.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications.

What is claimed is:

1. A diagnostic system for determining accuracy of a temperature-measuring system of a device for determining analyte concentrations in fluid samples, the diagnostic system comprising:
   a receiving port for receiving a test sensor, the test sensor including a fluid-receiving area containing a reagent that produces a measurable reaction with an analyte in a fluid sample;
   a reference object at least partially located proximate the receiving port during temperature measurements, the reference object including at least one of a resistor or a light emitting diode (LED); and
   a processing system configured to execute instructions embedded on a computer-readable medium, the instructions including the acts of:
      applying a current to the reference object until the reference object achieves a reference temperature,
      determining at least one test temperature for the reference object based on temperature measurements by the temperature-measuring system after the reference object achieves the reference temperature, and
      determining the accuracy of the temperature-measuring system by comparing the at least one test temperature to the corresponding reference temperature.

2. The diagnostic system of claim 1, wherein the temperature-measuring system includes a plurality of temperature-measuring systems disposed at different locations within the device for determining analyte concentrations in fluid samples.

3. The diagnostic system of claim 1, wherein the determining the accuracy of the temperature-measuring system includes comparing the reference temperature to a plurality of test temperatures determined after the reference object achieves the reference temperature.

4. A diagnostic system for determining accuracy of a temperature-measuring system of a device for determining analyte concentrations in fluid samples, the device including a receiving port for test sensors and a measurement system for measuring reactions between a reagent and analyte, the diagnostic system comprising:
   a reference object at least partially located proximate a receiving port during temperature measurements; and
   a processing system configured to execute instructions embedded on a computer-readable medium, the instructions including the acts of:
      applying a current to the reference object until the reference object achieves a reference temperature,
      determining at least one test temperature for the reference object based on temperature measurements by the temperature-measuring system after the reference object achieves the reference temperature, and
      determining the accuracy of the temperature-measuring system by comparing the at least one test temperature to the corresponding reference temperature.

5. The diagnostic system of claim 4, wherein the reference object includes at least one of a resistor or a light emitting diode (LED).

6. The diagnostic system of claim 4, wherein the reference object includes a resistor, the resistor being configured to receive the applied current to achieve the at least one reference temperature.

7. The diagnostic system of claim 4, wherein the reference object is removably insertable into the receiving port for the test sensors.

8. The diagnostic system of claim 4, further comprising a cooling element configured to cool the reference object to the reference temperature.

9. The diagnostic system of claim 4, wherein the temperature-measuring system includes a plurality of temperature-measuring systems disposed at different locations within a device for determining analyte concentrations in fluid samples.

10. The diagnostic system of claim 4, wherein the determining the accuracy of the temperature-measuring system includes comparing the reference temperature to a plurality of test temperatures determined after the reference object achieves the reference temperature.

11. The diagnostic system of claim 4, wherein the instructions further include the acts of calibrating the temperature-measuring system based on determined accuracy of the temperature-measuring system.

12. The diagnostic system of claim 11, wherein the calibrating occurs at a time after the manufacture and assembly of the device.

13. The diagnostic system of claim 11, wherein the determining the accuracy and the calibrating occur automatically on a periodic basis.

14. The diagnostic system of claim 11, wherein the calibrating includes correcting for one or more offset or gain errors associated with a signal generated by a temperature sensor of the temperature-measuring system.

15. A diagnostic system for determining accuracy of a temperature-measuring system of a device for determining analyte concentrations in fluid samples, the device including a receiving port for test sensors and a measurement system for measuring reactions between a reagent and analyte, the diagnostic system comprising:
   a reference object at least partially located proximate the receiving port during temperature measurements; and
   a processing system configured to execute instructions embedded on a computer-readable medium, the instructions including the steps of:
      applying a current to the reference object until the reference object achieves a reference temperature,
      determining a test rate of temperature change of the reference object based on at least one test temperature of the reference object determined via the temperature measuring system, and
      determining the accuracy of the temperature-measuring system based on the at least one test temperature measurement of the reference object by comparing the test rate of temperature change to an expected rate of temperature change for the reference object.

16. The diagnostic system of claim 15, wherein the reference object includes at least one of a resistor or a light emitting diode (LED).

17. The diagnostic system of claim 15, further comprising a cooling element configured to cool the reference object to the reference temperature.

18. The diagnostic system of claim 15, wherein the temperature-measuring system includes a plurality of temperature-measuring systems disposed at different locations within a device for determining analyte concentrations in fluid samples.

19. The diagnostic system of claim 15, wherein the determining the accuracy of the temperature-measuring system includes comparing the reference temperature to a plurality of test temperatures determined after the reference object achieves the reference temperature.

20. The diagnostic system of claim 15, wherein the instructions further include the acts of calibrating the temperature-measuring system based on determined accuracy of the temperature-measuring system.

* * * * *